United States Patent
Tasaki et al.

[11] Patent Number: 6,037,485
[45] Date of Patent: Mar. 14, 2000

[54] CVD PRECURSORS AND FILM PREPARATION METHOD USING THE SAME

[75] Inventors: Yuzo Tasaki; Mamoru Sato, both of Haichioji; Shuji Yoshizawa, Tokyo, all of Japan

[73] Assignee: Dowa Mining Co., Ltd., Tokyo, Japan

[21] Appl. No.: 09/327,417

[22] Filed: Jun. 8, 1999

Related U.S. Application Data

[62] Division of application No. 09/048,063, Mar. 26, 1998.

[30] Foreign Application Priority Data

Mar. 28, 1997 [JP] Japan ..................................... 9-092776

[51] Int. Cl.$^7$ ............................... C07F 3/00; C23C 16/00
[52] U.S. Cl. ............................... 556/1; 106/1.22; 427/252
[58] Field of Search ............................... 556/1; 106/1.22; 427/252

[56] References Cited

U.S. PATENT DOCUMENTS 5,090,985  2/1992  Soubeyrand et al. .................. 65/60.52

*Primary Examiner*—Porfirio Nazario-Gonzalez
*Attorney, Agent, or Firm*—McDerwott, Will & Emery

[57] ABSTRACT

A CVD precursor that is a precursor in film preparation by the CVD method, comprising a metalorganic compound containing a metal element constituting the film (called "main compound") having blended therewith another organic compound, the other organic compound having a lower vapor pressure than the main compound at a precursor vaporization temperature and when blended with the main compound forming a fusible blend having a lower melting point than the melting point of the main compound. In particular, when the main compound has the structural formula Ma(DPM)$_2$ (Ma being representing an alkaline earth metal), Ma(TMOD)$_2$ or Ma(TMND)$_2$ is blended therewith.

9 Claims, 5 Drawing Sheets

CVD PRECURSORS AND FILM PREPARATION METHOD USING THE SAME

This application is a divisional of application Ser. No. 09/048,063 filed Mar. 26, 1998, now allowed.

TECHNICAL FIELD

This invention relates to precursors for the chemical vapor deposition method (CVD method) that enable stable supply of precursor vapor during thin film preparation by the CVD method.

BACKGROUND ART

As is well known, processes for preparation of single crystal thin film, polycrystalline thin film and the like are of two types: dry processes and wet processes. A dry process is more often used, however, since the thin film prepared by a dry process is generally superior from the aspect of quality to that by a wet process.

Dry processes include physical film preparation techniques such as the vacuum deposition method, the ion plating method and the sputtering method and chemical film preparation techniques such as the chemical vapor deposition method (CVD method). Among these, the latter CVD method is widely employed because it is suitable for mass production owing not only to the fact that deposition rate control is easy but also to the fact that film preparation need not be conducted under high vacuum and, moreover, that high-speed film preparation is possible.

In the CVD method, a metalorganic complex is used as the precursor compound. In the case of decomposing the vapor thereof to form a metal thin film or the like, the thermo-CVD method, photo-CVD method or plasma-CVD method is adopted. Particularly in the cases of preparing the ferroelectric materials important in the development of recent memories such as the DRAM and FRAM and preparing the oxide thin films of the sub-electrode etc. constituting the underlayers thereof, the complex used as the precursor has generally been a metalorganic complex whose organic portion (ligand) is dipivaloylmethane, a kind of β-diketone. This is a dipivaloylmethane (DPM) chelate of M divalent metal represented as $M(DPM)_2$, where M is a divalent metal.

Since the melting point of such a metalorganic complex is generally high, however, the precursor vapor has to be generated by sublimation from the solid. In the case of a metalorganic complex whose melting point is higher than 200° C., for example, the operating devices of the exhaust system (automatic vacuum valves in the tubing, for example) must be made of a material that can withstand temperatures above 200° C. Fabrication of a mass production apparatus of this type is difficult with current technology. In view of equipment requirements, therefore, vaporization from solid state below the melting point is unavoidable.

In vaporization from a solid precursor, however, since it is difficult to generate gas of saturated vapor pressure for film preparation, a problem arises that the amount of precursor vapor obtained varies with change in precursor surface area. In other words, the surface area of a continuously used solid precursor decreases because of diminishing quantity and condensation of the precursor in the source vessel, resulting in a gradual lowering of the vaporization rate. This is particularly impractical in multi-element system thin film preparation because the decrease in vaporization rate causes variation in composition.

A need has therefore been felt for development of precursor compounds that can be vaporized from liquid state. This is because a liquid precursor readily provides a precursor gas of saturated vapor pressure when bubbled and does not give rise to difference in deposition rate owing to time-course change in the amount of precursor in the vessel.

By use of some β-diketones other than DPM as ligand, we earlier developed CVD precursor compounds (metalorganic complexes) containing Cu, Pb, Y, Nd, Ru, Ir etc. that have much lower melting points than DPM complexes and can be used in liquid state. However, with regard to the alkaline earth metals, which are important constituent elements of ferroelectric thin films, oxide superconducting thin films and so forth, virtually no metalorganic complexes with characteristics superior to the corresponding DPM complexes are known.

On the other hand, when ferroelectric materials such as $(Ba, Sr)TiO_3$ (BST) and $SrBi_2Ta_2O_9$ (SBT) are prepared by the CVD method, securement of a uniform high deposition rate by high quality vaporization of the Ba, Sr or other precursor compound is indispensable. A liquid source CVD method has therefore recently been developed in which, even when using an alkaline earth DPM complex as the precursor compound, the precursor compound (the DPM complex) is once dissolved in a solvent, the solution is fed to the vaporizer under flow control by a fluid mass flow controller, and the whole amount, including the solvent, is instantaneously vaporized.

OBJECT OF THE INVENTION

Although the principle of the liquid source CVD method should enable easy composition control, problems actually arise in practice, such as that precursor compound decomposes before vaporizing or that the vaporization rate is reduced owing to a rise in the pressure within the system caused by accretion in the tubing of decomposed matter remaining in the vaporizer.

Although methods have also been proposed for enhancing the volatility of DPM complexes by adding a substance such as tetraethylenepentamine or tetraglyme to lower the melting point, these adducts are released from the precursor compound by heating and the like. Since the released substance alone has high volatility and evaporates before the precursor compoumds, a problem of varying volatility and melting point arises.

Although a metalorganic complex synthesized by using such as hexaflouroacetylacetone as a ligand containing fluorine in the molecule has a low melting point and high vapor pressure, use thereof as a precursor compound is liable to lead to inclusion of fluorine as an impurity in the prepared film, and this results in pronounced degradation of the film properties.

The object of this invention is therefore to secure low-melting-point CVD precursors capable of overcoming the aforesaid problems and, in particular, to provide CVD precursors that enable alkaline earth precursor compounds to be vaporized from liquid state.

DISCLOSURE OF THE INVENTION

This invention provides a CVD precursor that is a precursor in film preparation by a CVD method, comprising a metalorganic compound containing a metal element constituting the film (called "main compound") having blended therewith another organic compound containing a metal element constituting the film, the other organic compound having a lower vapor pressure than the vapor pressure of the main compound at a precursor vaporization temperature and when blended with the main compound forming a fusible blend having a lower melting point than the melting point of the main compound.

This invention further provides, in a film preparation method by a CVD method using a metalorganic compound (called "main compound") as a precursor compound for vaporization, a film preparation method according to the CVD method characterized in heating a blend that is obtained by blending the main compound with another organic compound having a lower vapor pressure than the vapor pressur of the main compound at a precursor vaporization temperature (hereinafter "use temperature") and having a lower melting point than the main compound to a temperature not higher than the melting point of the main compound, thereby causing the blend to be in a molten state, and vaporizing the main compound from this molten state.

This invention further provides a CVD precursor that is a CVD precursor substance used to deposit an alkaline earth metal or a substance containing an alkaline earth metal by a CVD method, comprising a β-diketonate composed of a dipivaloylmethane (DPM) chelate of Ma having dipivaloylmethane as ligands of Ma and represented by the general formula Ma(DPM)$_2$ having blended therewith a β-diketonate composed of a (TMOD) chelate or a (TMND) chelate of Ma having 2,2,6,6-tetramethyl-3,5-octanedione or 2,2,6,6-tetramethyl-3,5-nonanedione as ligands of Ma and represented by the general formula Ma(TMOD)$_2$ or Ma(TMND)$_2$, where Ma is an alkaline earth metal.

BEST MODE FOR CARRYING OUT THE INVENTION

Figure 1:
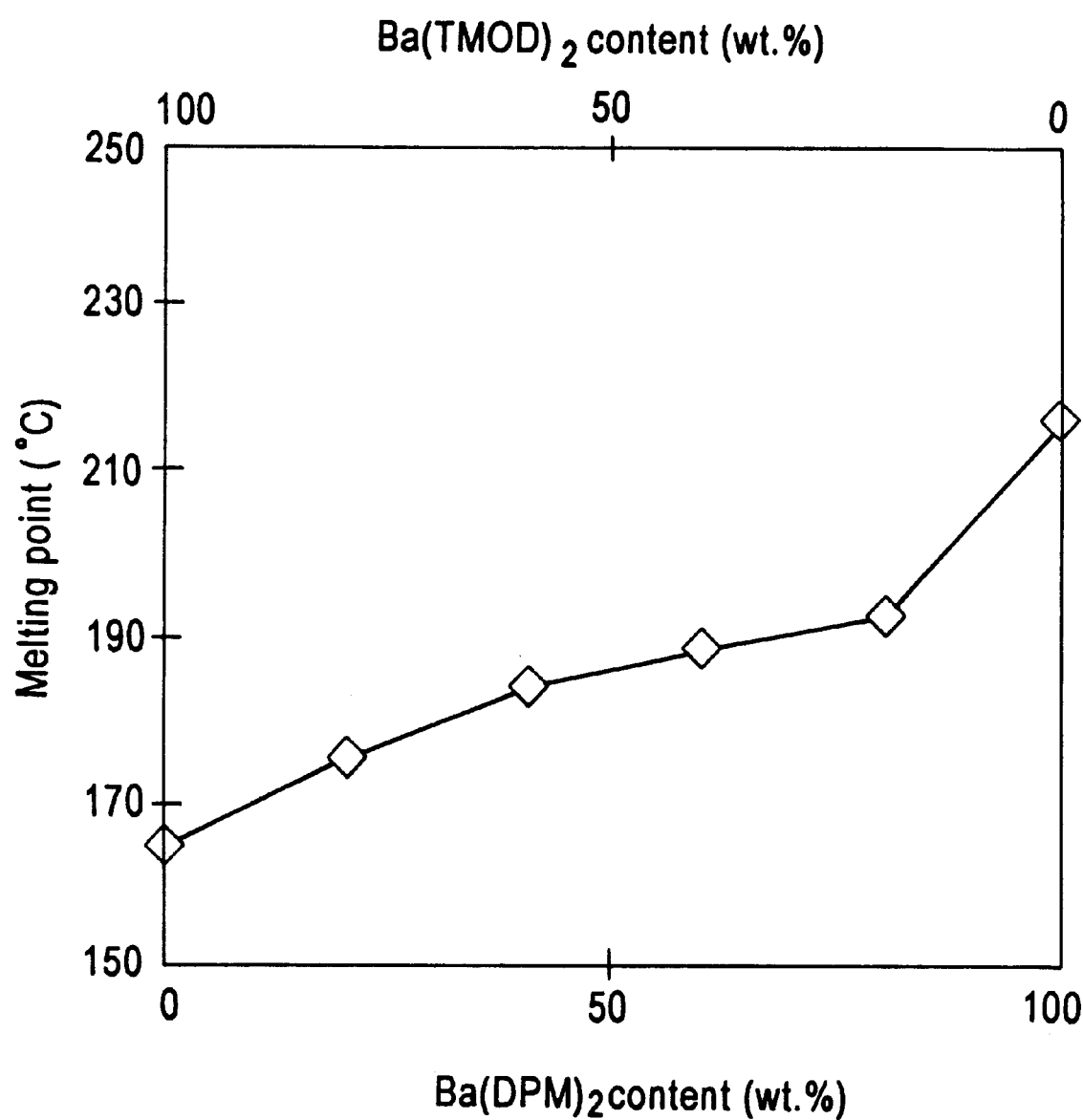
FIG. 1 shows the relationship between the blending ratio of Ba(DPM)$_2$ and Ba(TMOD)$_2$ and the melting point of the blend.

Through research focused on overcoming the aforesaid problems, the inventors discovered that even a CVD precursor compound with a high melting point that has had to be used in solid state can be used in liquid state when made co-present with another organic compound having a given relationship therewith. Specifically, we discovered regarding the CVD method using a metalorganic compound as the precursor compound to be vaporized that when another organic compound that has a lower vapor pressure at the use temperature than the metalorganic compound (main compound) and that melts eutectically with the main compound is made co-present with main compound, a liquid state is obtained at a temperature at or below the melting point of the main compound and the vaporization can be effected from this liquid state. It is essential for the other organic compound made co-present to have a lower vapor pressure at the use temperature than the main compound and to from a mutually intermixed melt therewith.

For example, regarding the case where an alkaline earth metal or a substance containing an alkaline earth metal is to be deposited using as the precursor for vaporization by the CVD method one whose main compound is a Ma dipivaloylmethanate (Ma being an alkaline earth metal) represented by the general formula Ma(DPM)$_2$, it was learned that when the precursor for vaporization is prepared by blending an appropriate amount of Ma(TMOD)$_2$ or Ma(TMND)$_2$ with the Ma(DPM)$_2$, good vaporization from the molten state of this blend is possible and, accordingly, the problems mentioned earlier can be overcome.

When the alkaline earth metal Ma is barium or strontium, Ma(TMOD)$_2$ is represented by Ba(TMOD)$_2$ or Sr(TMOD)$_2$ and Ma(TMND)$_2$ is represented by Ba(TMND)$_2$ or Sr(TMND)$_2$; provided, however, that, (TMOD) represents the monovalent negative ion portion of 2,2,6,6-tetramethyl-3,5-octanedione removed of one hydrogen atom and (TMND) represents the monovalent ion portion of 2,2,6,6-tetramethyl-3,5-nonanedione removed of one hydrogen atom. The organometallic complexes Ba(TMOD)$_2$, Sr(TMOD)$_2$, Ba(TMND)$_2$ and Sr(TMND)$_2$ are thought to be compounds newly discovered by the inventors.

Ba(TMOD)$_2$ is a β-diketone represented by the following structural formula, which becomes the structural formula of Sr(TMOD)$_2$ when Ba is replaced by Sr.

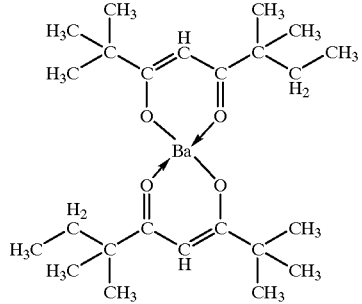

The melting point of Ba(TMOD)$_2$ is about 165° C., approximately 50° C. below Ba(DPM)$_2$'s melting point of about 217° C. The melting point of Sr(TMOD)$_2$ is about 200° C., approximately 20° C. below Sr(DPM)$_2$'s melting point of about 220° C.

Ba(TMOD)$_2$ or Sr(TMOD)$_2$ can be obtained by the method of dissolving metallic barium or metallic strontium and 2,2,6,6-tetramethyl-3,5-octanedione as ligand in a solvent such as toluene under heating and stirring, removing the solvent from the solution by distillation under reduced pressure, and purifying the precipitated solid component (e.g., sublime it after reduced-pressure drying).

Change in the melting point of blended Ba(DPM)$_2$ and Ba(TMOD)$_2$ with change in blending ratio (by weight) was investigated and the results are shown in FIG. 1. At all blending ratios the two compounds form a uniformly intermixed melt when heated to the molten state and the melting point of the blend is lower than that of Ba(DPM)$_2$ alone. For instance, the melting point at a blending ratio of Ba(DPM)$_2$/Ba(TMOD)$_2$=8/2 is about 193° C., and the vapor pressure of Ba(TMOD)$_2$ is lower than that of Ba(DPM)$_2$ in a molten state at or below 200° C. No particular phenomenon of only the Ba(TMOD)$_2$ evaporating preferentially therefore arises.

Figure 2:
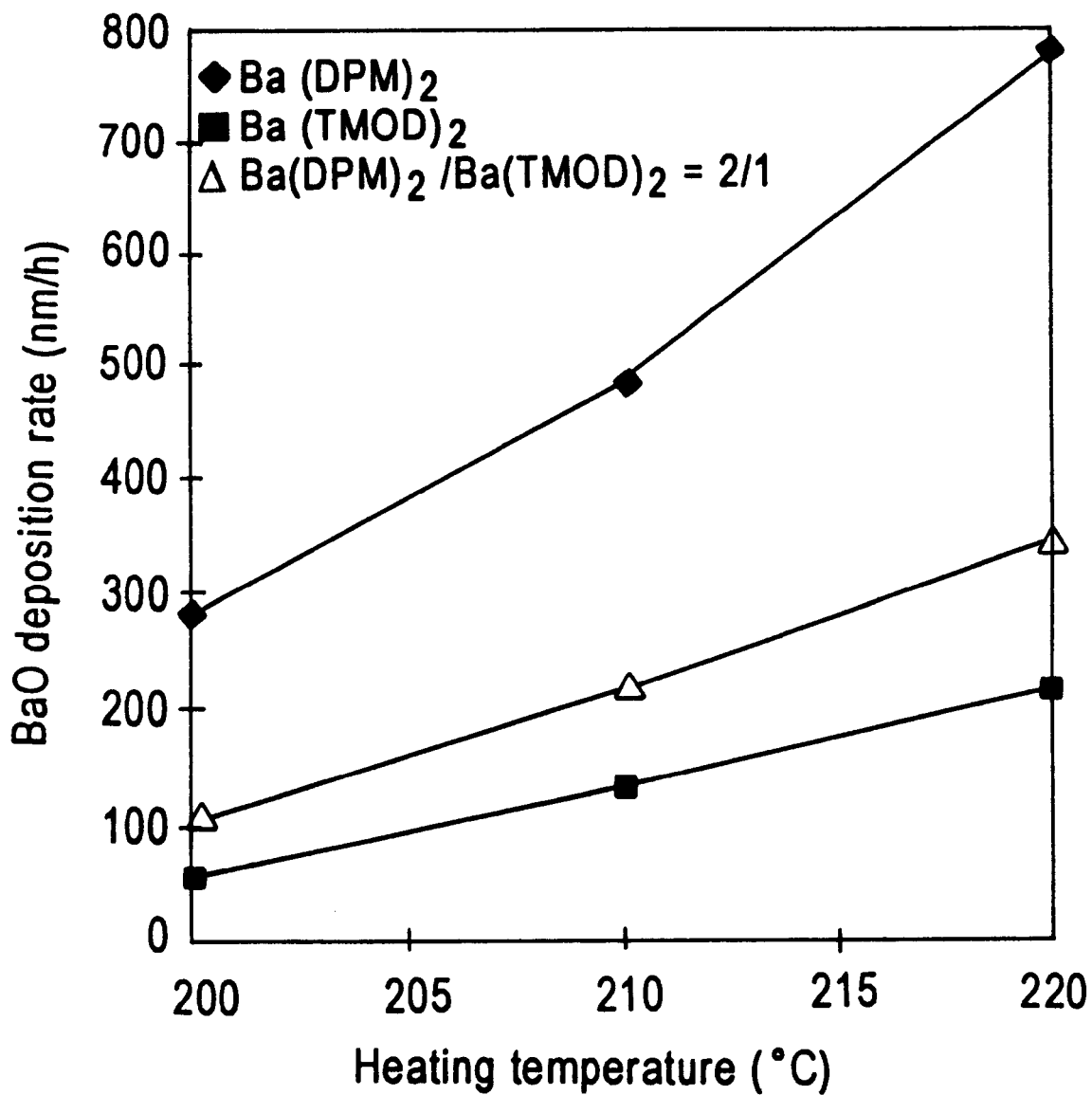
FIG. 2 shows the relationship between heating temperature and BaO deposition rate for Ba(DPM)$_2$, Ba(TMOD)$_2$ and a blend thereof.

FIG. 2 shows heating temperature vs BaO deposition rate when BaO film was prepared under the conditions of Example 1 set out later using a blend of Ba(DPM)$_2$ and Ba(TMOD)$_2$, in comparison with the cases of using Ba(DPM)$_2$ alone and Ba(TMOD)$_2$ alone. Specifically, the Δ marks in FIG. 2 show the relationship between heating temperature (thermostatic chamber temperature) and deposition rate for a precursor blended of Ba(DPM)$_2$ and Ba(TMOD)$_2$ at a ratio of 2:1 (melting point≈190° C.). The blend was in molten state over the whole heating temperature range (200–220° C.) in the drawing. Vaporization from the liquid state of this blend is therefore possible even at, for example, 200° C. In contrast, although the deposition rate with Ba(DPM)$_2$ alone at 200° C. is fast (♦ marks in the drawing), the problems set forth earlier arise because the vaporization is from solid state. Although with Ba(TMOD)$_2$ alone vaporization from liquid state is possible at 200° C. (■ marks in the drawing), the deposition rate is slower than with the blend (Δ marks). Specifically, the vapor pressure of Ba(TMOD)$_2$ is low, so that even though it can by itself be vaporized from molten state at a low temperature, the deposition rate is lower than in the case of the blend. This shows that in the molten state of the blend, no particular phenomenon of only the Ba(TMOD)$_2$ evaporating preferentially arises.

This characteristic behavior seen in the case of blends of Ba(DPM)$_2$ and Ba(TMOD)$_2$ is substantially the same in the case of blends of Sr(DPM)$_2$ and Sr(TMOD)$_2$. The same can also be said blends of Ba(DPM)$_2$ and Sr(TMOD)$_2$ and blends of Sr(DPM)$_2$ and Ba(TMOD)$_2$.

On the other hand, Sr(TMND)$_2$ is a β-diketonate represented by the following structural formula, which becomes the structural formula of Ba(TMND)$_2$ when Sr is replaced by Ba.

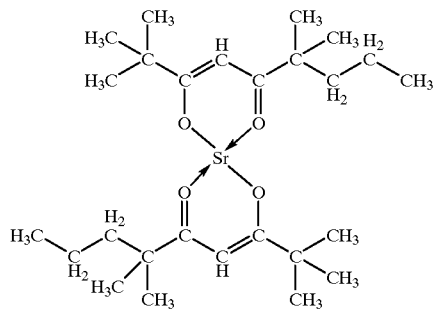

The melting point of Sr(TMND)$_2$ is about 179° C., approximately 40° C. below Sr(DPM)$_2$'s melting point of about 200° C. The melting point of Ba(TMND)$_2$ is about 145° C., approximately 70° C. below Ba(DPM)$_2$'s melting point of about 217° C.

Sr(TMND)$_2$ or Ba(TMND)$_2$ can be obtained by the method of dissolving metallic strontium or metallic barium and 2,2,6,6-tetramethyl-3,5-nonanedione as ligand in a solvent such as toluene under heating and stirring, removing the solvent from the solution by distillation under reduced pressure, and purifying the precipitated solid component (e.g., subliming it after reduced-pressure drying).

Figure 3:
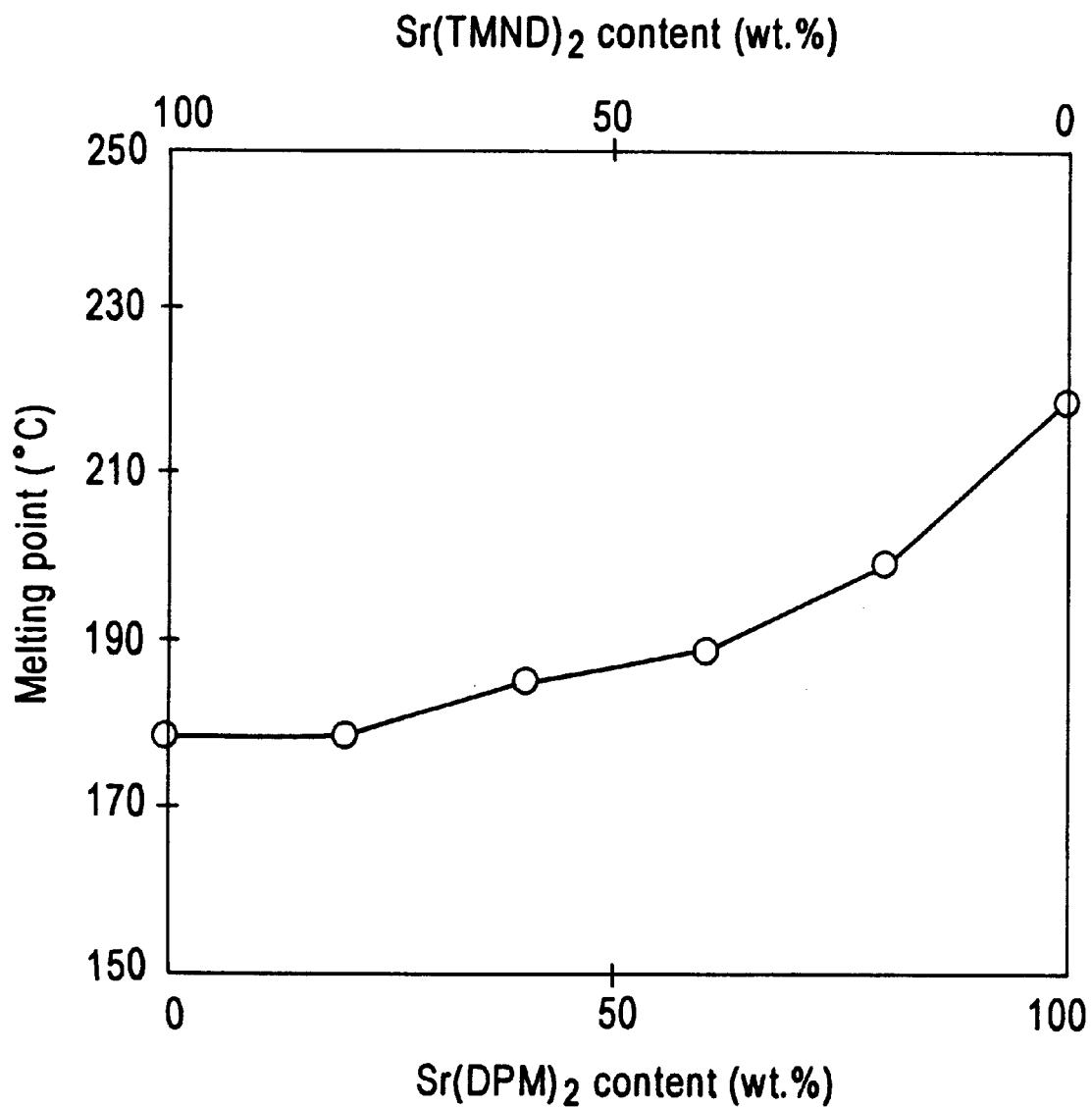
FIG. 3 shows the relationship between the blending ratio of Sr(DPM)$_2$ and Sr(TMND)$_2$ and the melting point of the blend.

Blending Sr(TMND)$_2$ and Sr(DPM)$_2$ enables formation of a uniform fusible substance having a lower melting point than Sr(DPM)$_2$. The change in the melting point with change in the blending ratio of the blend is shown in FIG. 3. When this blend is used, vaporization from the molten state is possible at a lower heating temperature than in the case of Sr(DPM)$_2$ alone, and since the vapor pressure of Sr(TMND)$_2$ in this state is low, no particular phenomenon arises of only the Sr(TMND)$_2$ evaporating preferentially. Like in the case of using Ba(TMOD)$_2$, therefore, by use of this blend as a CVD precursor substance, vaporization from liquid state can be achieved at a lower heating temperature than when using Sr(DPM)$_2$ alone and Sr or a Sr-containing substance can be deposited at a rapid deposition rate.

Stated generally, this means that, denoting the metal element of the film to be prepared as element M, the CVD precursor for preparing a film of element M or containing element M can be reduced to a lower melting point than that of the metalorganic compound containing element M (main compound) and, moreover, by blending the main compound with an appropriate amount of another organic compound whose vapor pressure at the use temperature is lower than that of the main compound, vaporization from the liquid state (temperature not higher than the melting point of the main compound), impossible with the main compound alone, can be effected, so that the evaporation rate in this case can be made faster than that of the other organic compound. In implementing the CVD method, therefore, vaporization of even a metalorganic complex which heretofore could only be vaporized (sublimed) from solid state owing to its high melting point can be vaporized from liquid state.

The other organic compound having a lower vapor pressure at the use temperature than the main compound and usable to obtain a blend having a lower melting point than the main compound can be another metalorganic compound containing the same element M as the main compound or can be a metalorganic compound containing an element different from the element M. In the latter case, it can be advantageously employed to obtain a composite prepared film of the element M and another element. Although the other organic compound for blending preferably does not react with the main compound, one that reacts therewith is usable insofar as it does produce an irreversible reaction with the main compound that completely eliminates the presence of the main compound. The other organic compound used for blending need not necessarily be of one type; blending of two or more types is also possible.

As the other organic compound for blending, any type can be used, even one having a higher melting point than the melting point of the main compound, insofar as it has a lower melting point than the main compound when blended with the main compound and, moreover, has a lower vapor pressure than the main compound at the use temperature. When a type of lower melting point than the main compound is used, however, the melting point of the blend does not rise even if the blend ratio in the blend changes during use. This is advantageous in the point that the precursor can be used up in the liquid state.

The main compound used in implementing the invention is typically a metalorganic complex having a β-diketone ligand, which is particularly advantageous when the metal in the metalorganic complex is an alkaline earth metal. Although the other organic compound for blending also has a β-diketone ligand, it can be a metalorganic complex having a ligand that is different from the organic ligand of the main compound. Specific examples include cases where the metalorganic complex for blending is Ma(TMOD)$_2$ or Ma(TMND)$_2$ when the main compound is Ma(DPM)$_2$, Ma being an alkaline earth metal as set out earlier.

As seen with Ma(DPM)$_2$, for example, ordinarily used alkaline earth metalorganic complexes have generally been vaporized from solid state because even those with high vapor pressure (high deposition rate) have high melting points. However, the time-course change in surface area with progressive vaporization from solid state makes it impossible to maintain a constant state. This invention enables the preparation of films of alkaline earth metal-containing substances, which has heretofore had to rely on such vaporization from solid state, to be effected from molten state to obtain a large amount of vapor stably. When applied to the preparation of films containing multiple elements, moreover, the invention enables fabrication of thin films of constant compositions determined by the saturated vapor pressures. Typical alkaline earth metals include Ca, Sr and Ba.

Thus, in accordance with the invention, even CVD precursor compounds which have unavoidably been vaporized from solid state can be vaporized from liquid state by lowering their melting points. Since saturated vapor of the precursor compound is easy to obtain in the liquid state, the amount of vapor generated does not vary, a uniform deposition rate is obtained, and a faster deposition rate can be secured than by sublimation from a solid that is hard to vaporize at saturated vapor pressure. Especially if bubbling is effected, the deposition rate becomes even more rapid. Compared with the deposition rates in the non-bubbled state shown by the data of FIG. 2, for example, the deposition rate of BaO increased to 744 nm/h when a 2-to-1 blend of $Ba(DPM)_2$ and $Ba(TMOD)_2$ (melting point≈190° C.) was bubbled at 200° C.

Figure 4:
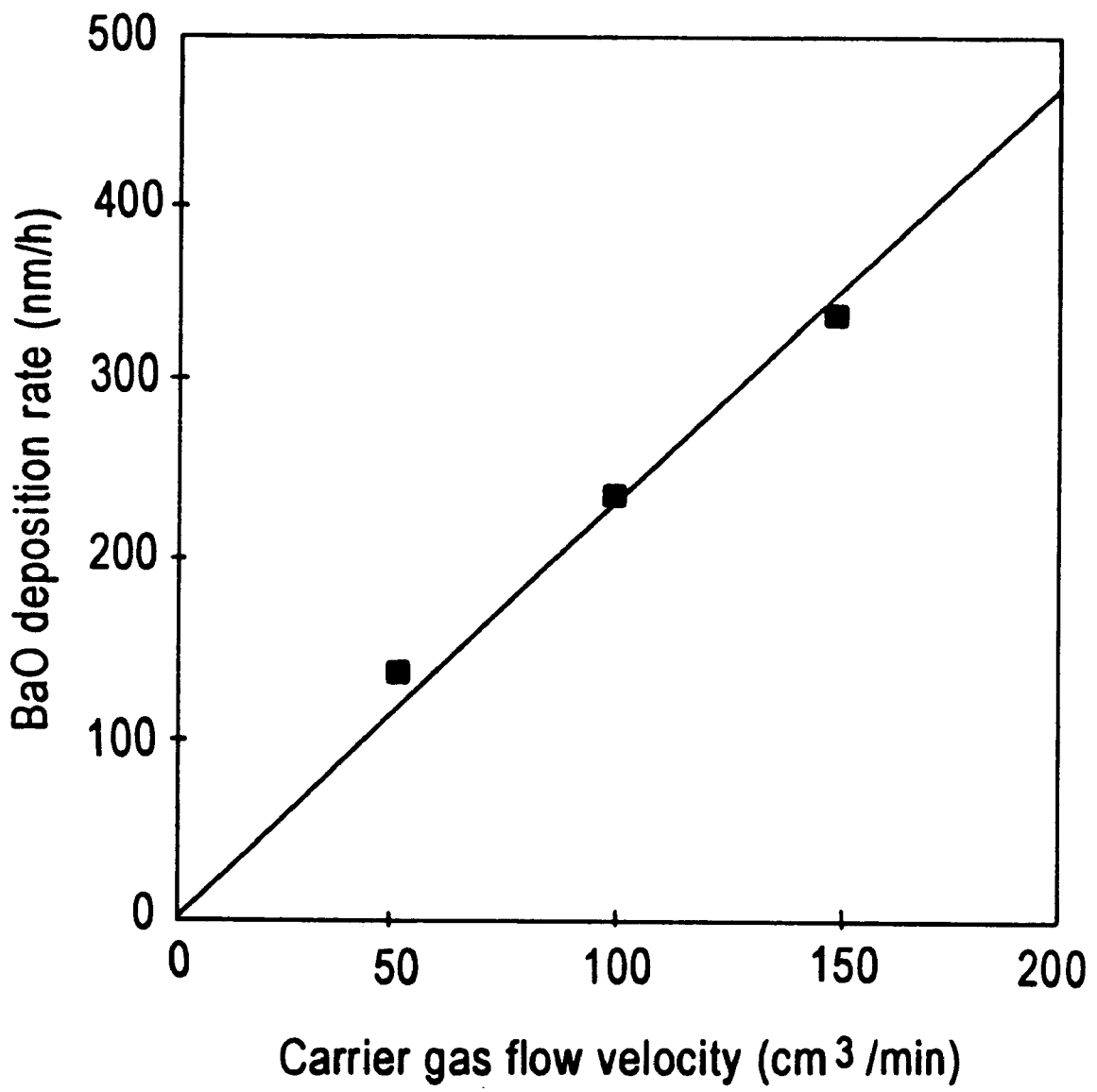
FIG. 4 shows the relationship between carrier gas flow rate and deposition rate when a CVD precursor substance is vaporized from liquid state.

In vaporization from liquid state, the vaporization rate is fast and the vapor pressure soon approaches saturation. When the vapor is transported by a carrier gas, therefore, the deposition rate can be increased merely by increasing the flow speed of the carrier gas supplied to the evaporation interface of the liquid precursor. FIG. 4 shows change in BaO deposition rate with change in the flow rate (bubbling flow rate) of argon gas contacted with a liquid precursor of the same type as that in Example 1 set out later, under conditions of a precursor temperature of 200° C., an oxygen flow rate of 200 milliliter/min, a total argon gas flow rate of 200 milliliter/min, a substrate temperature of 500° C. and a reaction pressure of 12.5 torr. As can be seen from FIG. 4, the faster the flow rate of the carrier gas contacted with the liquid precursor (shown on the lateral axis as the flow velocity) is made, the faster is the deposition rate obtained.

For preparing the precursor blend of the invention, there can be adopted, for example, the method of dissolving the main compound and the other organic compound for blending in a solvent and distilling off the solvent, the method of melting the blend by heating to or above the melting point of the other substance, or the method of synthesizing the individual substances by conducting synthesis under such conditions that produce two or more substances.

Figure 5:
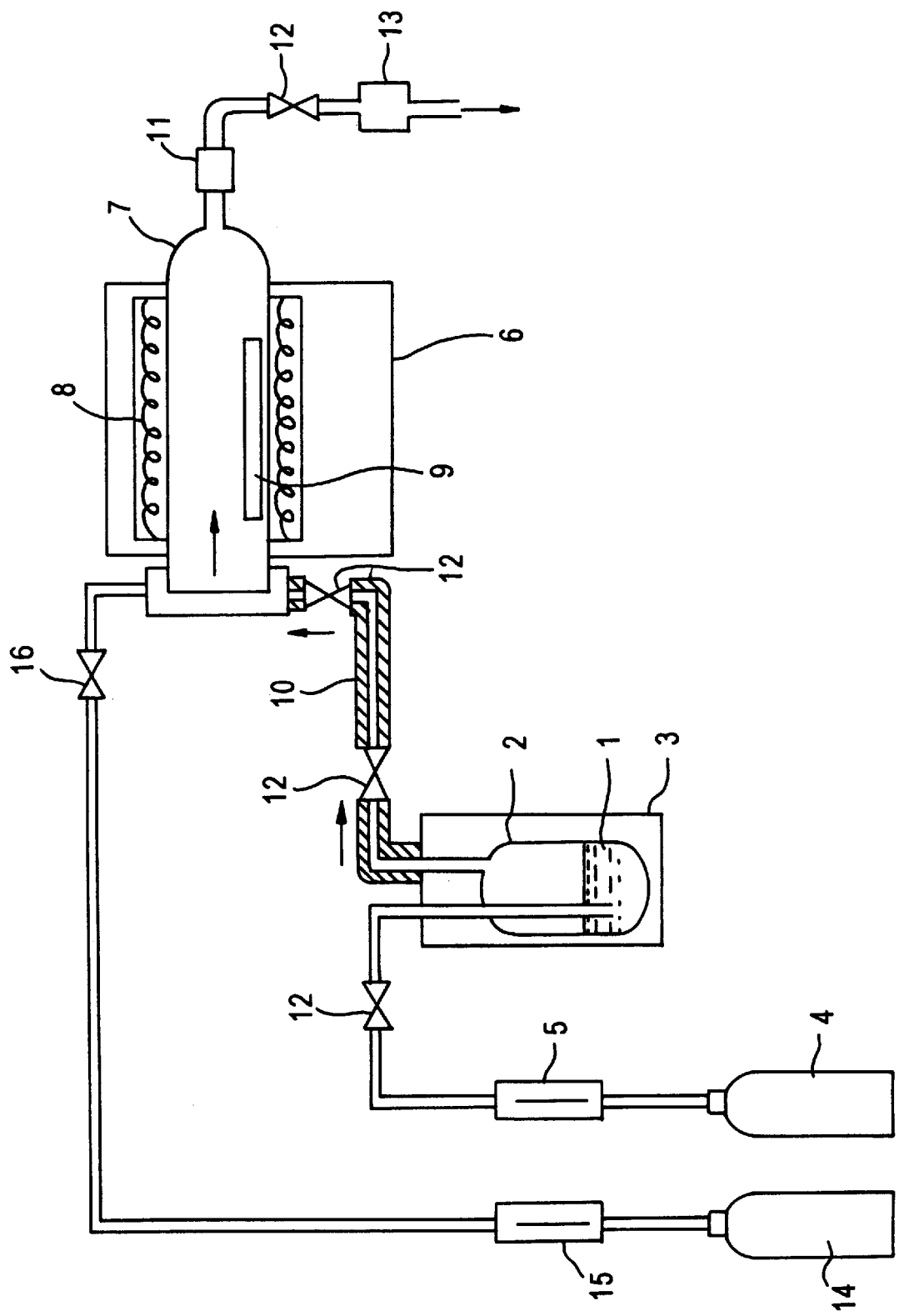
FIG. 5 is an equipment layout diagram showing an example of a setup for implementing the thermo-CVD method.

As shown by way of example in FIG. 5, for using the blended precursor to prepare thin film by the CVD method, a source vessel 2 containing precursor 1 is maintained at a prescribed temperature in a thermostatic chamber and an inert carrier gas (e.g., argon gas) 4 is introduced into the source vessel 2 under flow rate regulation by a flow meter 5 to generate a gas flow entraining the precursor compound from the source vessel 2.

The precursor compound vapor generated in this manner is led into the reaction tube 7 of a thermal decomposition furnace 6. The reaction tube (e.g., a quartz tube) 7 is heated by a heater 8 to maintain a substrate 9 placed in the tube at a prescribed temperature (e.g., 300–800° C.), thereby thermally decomposing the precursor compound and depositing a substance containing part of the constituent elements of the precursor compound on the substrate 9 to form a film. The line from the source vessel 2 to the thermal decomposition furnace 6 is preferably maintained at a temperature higher than the heating temperature in the source vessel by a heat insulating layer 10 or a heating and heat insulating means so as to prevent condensation. The exhaust gas leaving the reaction tube 7 is discharged through a cold trap 11. In FIG. 5, 12 denotes valves and 13 a rotary pump.

EXAMPLES

Example 1

Bis(2,2,6,6-tetramethyl-3,5-heptanedionato) barium, i.e., $Ba(DPM)_2$, (melting point: 217° C.) and bis(2,2,6,6-tetramethyl-3,5-octanedionato) barium, i.e., $Ba(TMOD)_2$, (melting point: 165° C.) were blended at a weight ratio of 8:2 in an inert gas atmosphere to obtain a blend with a melting point of 193° C.

The $Ba(TMOD)_2$ was produced as follows. First, in a nitrogen atmosphere, 150 milliliters of toluene was added to 6.4 g of metallic barium, the mixture was added with 45 g of 2,2,6,6-tetramethyl-3,5-octanedione and stirred at 120° C., the solvent and excess 2,2,6,6-tetramethyl-3,5-octanedione were distilled off under reduced pressure after the metallic barium had completely dissolved, and purification by sublimation was effected after reduced-pressure drying to afford 8.5 g of $Ba(TMOD)_2$ as powder.

The 8:2 blend of $Ba(DPM)_2$ and $Ba(TMOD)_2$, still in powder state, was charged into the stainless steel source vessel 2 of the CVD apparatus of FIG. 5 as a CVD precursor, whereafter film preparation operation was effected on a silicon substrate used as the substrate 9.

At this time, 10 g of the precursor was charged into the source vessel 2 and the thermostatic chamber 3 was set to maintain a constant temperature of 195° C. With the silicon substrate 9 maintained at 500° C. by the heater 8, argon gas was passed as carrier gas at 100 ml/min and bubbled in the precursor. The generated precursor compound vapor was led to the quartz reaction tube 7. The line from the vessel 2 to the thermal decomposition furnace 6 was maintained at 200° C. by heat retention. Oxygen gas from an oxygen source 14 was added into the reaction tube 7 through a flow meter 15 and a valve 16 at a flow rate of 100 ml/min.

When film preparation operation was conducted for 30 min under these conditions, there was obtained a 3,000-angstrom-thick uniform barium oxide thin film.

Film preparation operation was repeated under completely the same conditions as the foregoing except that the amount of blended precursor charged in the source vessel 2 was changed to 20 g. A 3,000-angstrom-thick uniform barium oxide thin film was also obtained in this case. That is, the thickness of the formed film was the same even though the amount of precursor charged into the source vessel 2 was doubled. This shows that the amount of vapor from the precursor compound is constant throughout the treatment period and, moreover, that the decomposed amount is also constant.

Comparative Example 1

Film preparation was conducted under the same conditions as in Example 1 except that only bis(2,2,6,6-tetramethyl-3,5-heptanedionato) barium was placed in the stainless steel source vessel 2, i.e., $Ba(DPM)_2$ was used alone. As a result, after 30 min the thickness of the barium oxide film obtained with 10 g of charged precursor was 1,000 angstrom and that obtained with 20 g of charged precursor was 1,400 angstrom. This shows that since the precursor in the vessel was in solid state, the amount of vapor varied over time as the surface area changed with changing volume. It also indicates that the amount of vapor obtained was lower because bubbling could not be conducted.

Example 2

Bis(2,2,6,6-tetramethyl-3,5-heptanedionato) barium, i.e., Ba(DPM)$_2$, (melting point: 217° C.) and bis(2,2,6,6-tetramethyl-3,5-octanedionato) strontium, i.e., Sr(TMOD)$_2$, (melting point: 200° C.) were blended at a weight ratio of 8:2 in an inert gas atmosphere to obtain a blend with a melting point of 205° C.

The Sr(TMOD)$_2$ was produced as follows. In a nitrogen atmosphere, 150 milliliters of toluene was added to 4.3 g of metallic strontium, the mixture was added with 45 g of 2,2,6,6-tetramethyl-3,5-octanedione and stirred at 120° C. for 24 hr, the undissolved metallic strontium was removed, the solvent and excess 2,2,6,6-tetramethyl-3,5-octanedione were distilled off under reduced pressure, and purification by sublimation was effected after reduced-pressure drying to afford 5.7 g of Sr(TMOD)$_2$ as powder.

The blend was charged into the stainless steel source vessel 2 of the CVD apparatus of FIG. 5 as a precursor, whereafter film preparation operation was effected on a silicon substrate used as the substrate 9.

At this time, 10 g of the blended precursor was charged into the source vessel 2 and the thermostatic chamber 3 was set to maintain a constant temperature of 210° C. With the silicon substrate 9 maintained at 500° C. by the heater 8, argon gas was passed as carrier gas at 100 ml/min and bubbled in the precursor. The generated precursor compound vapor was led to the quartz reaction tube 7. The line from the vessel 2 to the thermal decomposition furnace 6 was maintained at 220° C. by heat retention. Oxygen gas from an oxygen source 14 was added into the reaction tube 7 through the flow meter 15 and the valve 16 at a flow rate of 100 ml/min.

When film preparation operation was conducted for 30 min under these conditions, there was obtained a 4,000-angstrom-thick uniform barium/strontium oxide thin film. The Ba:Sr mol ratio of the obtained thin film was 6:4.

Film preparation operation was repeated under completely the same conditions as the foregoing except that the vessel 2 was charged with 10 g of a blend (melting point: 209° C.) obtained by blending bis(2,2,6,6-tetramethyl-3,5-heptanedionato) barium (melting point: 217° C.) and bis(2,2,6,6-tetramethyl-3,5-heptanedionato) strontium (melting point: 200° C.) at a weight ratio of 6:4 in an inert gas atmosphere.

A 4,000-angstrom-thick uniform barium/strontium oxide thin film was also obtained in this case. The Ba:Sr mol ratio of the obtained thin film was 6:4. That is, a formed film of the same thickness and the same composition was obtained even though the blending ratio of the blended precursor charged in the vessel 2 was changed. This shows that the amount of vapor from the precursor compound is constant throughout the treatment period and that saturated vapor of each compound is supplied.

Example 3

Bis(2,2,6,6-tetramethyl-3,5-heptanedionato) strontium, i.e., Sr(DPM)$_2$, (melting point: 220° C.) and bis(2,2,6,6-tetramethyl-3,5-nonanedionato) strontium, i.e., Sr(TMND)$_2$, (melting point: 179° C.) were blended at a weight ratio of 8:2 in an inert gas atmosphere to obtain a blend with a melting point of 199° C.

The Sr(TMND)$_2$ was produced as follows. In a nitrogen atmosphere, 150 milliliters of toluene was added to 4.3 g of metallic strontium, the mixture was added with 47 g of 2,2,6,6-tetramethyl-3,5-nonanedione and stirred at 120° C. for 24 hr, the undissolved metallic strontium was removed, the solvent and excess 2,2,6,6-tetramethyl-3,5-nonanedione were distilled off under reduced pressure, and purification by sublimation was effected after reduced-pressure drying to afford 5.3 g of Sr(TMND)$_2$ as powder.

The blend was charged into the stainless steel source vessel 2 in the CVD apparatus of FIG. 5 as a precursor, whereafter film preparation operation was effected on a silicon substrate used as the substrate 9.

At this time, 10 g of the blended precursor was charged into the source vessel 2 and the thermostatic chamber 3 was set to maintain a constant temperature of 200° C. With the silicon substrate 9 maintained at 500° C. by the heater 8, argon gas was passed as carrier gas at 100 ml/min and bubbled in the precursor. The generated precursor compound vapor was led to the quartz reaction tube 7. The line from the vessel 2 to the thermal decomposition furnace 6 was maintained at 210° C. by heat retention. Oxygen gas from an oxygen source 14 was added into the reaction tube 7 through the flow meter 15 and the valve 16 at a flow rate of 100 ml/min.

When film preparation operation was conducted for 30 min under these conditions, there was obtained a 5,000-angstrom-thick uniform strontium oxide thin film.

Film preparation operation was repeated under completely the same conditions as the foregoing except that the amount of blended precursor charged in the source vessel 2 was changed to 20 g. A 5,000-angstrom-thick uniform strontium oxide thin film was also obtained in this case. That is, the thickness of the formed film was the same even though the amount of precursor charged into the source vessel 2 was doubled. This shows that the amount of vapor from the precursor compound is constant throughout the treatment period and, moreover, that the decomposed amount is also constant.

Comparative Example 2

Film preparation was conducted under the same conditions as in Example 3 except that only bis(2,2,6,6-tetramethyl-3,5-heptanedionato) strontium was placed in the stainless steel source vessel 2, i.e., Sr(DPM)$_2$ was used alone. As a result, after 30 min the thickness of the strontium oxide film obtained with 10 g of charged precursor was 1,900 angstrom and that obtained with 20 g of charged precursor was 2,500 angstrom. This shows that since the precursor in the vessel was in solid state, the amount of vapor varied over time as the surface area changed with changing volume. It also indicates that the amount of vapor obtained was lower than in Example 3 because bubbling could not be conducted.

As explained in the foregoing, this invention improves the CVD film preparation method, which heretofore unavoidably required vaporization from solid state owing to high melting point, so that the precursor compound can be vaporized from liquid state to enable supply of saturated vapor and, as such, greatly contributes to thin film preparation technology useful for ferroelectric materials and the like through the effects of enabling a constant deposition rate, easy control of the deposition rate, and fast and uniform film preparation.

We claim:

1. A CVD precursor that is a precursor in film preparation by a CVD method, comprising a metalorganic compound containing a metal element constituting the film (called "main compound") having blended therewith another organic compound, the other organic compound having a lower vapor pressure than the vapor pressure of the main compound at a precursor vaporization temperature and when blended with the main compound forming a fusible blend having a lower melting point than the melting point of the main compound.

2. A CVD precursor according to claim 1, wherein the main compound is a metalorganic compound having a β-diketone ligand.

3. A CVD precursor according to claim 1, wherein the metal element of the main compound is an alkaline earth metal.

4. A CVD precursor that is a CVD precursor used to deposit an alkaline earth metal or a substance containing an alkaline earth metal by a CVD method, comprising a β-diketonate composed of a dipivaloylmethane (DPM) chelate of Ma having dipivaloylmethane as ligands of Ma and represented by the general formula Ma(DPM)$_2$ having blended therewith a β-diketonate composed of a (TMOD) chelate or a (TMND) chelate of Ma having 2,2,6,6-tetramethyl-3,5-octanedione or 2,2,6,6-tetramethyl-3,5-nonanedione as ligands of Ma and represented by the general formula Ma(TMOD)$_2$ or Ma(TMND)$_2$, where Ma is an alkaline earth metal.

5. A CVD precursor according to claim 4, wherein Ma is Ba or Sr.

6. A CVD precursor according to claim 4, wherein Ma(TMOD)$_2$ is Ba(TMOD)$_2$ or Sr(TMOD)$_2$.

7. A CVD precursor according to claim 4, wherein Ma(TMND)$_2$ is Sr(TMND)$_2$.

8. A CVD precursor that is a CVD precursor substance used to deposit Ba or a substance containing Ba and that has the following structural formula.

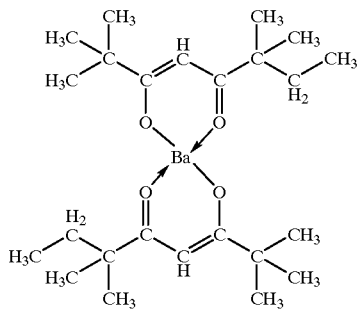

9. A CVD precursor that is a CVD precursor substance used to deposit Sr or a substance containing Sr and that has the following structural formula.

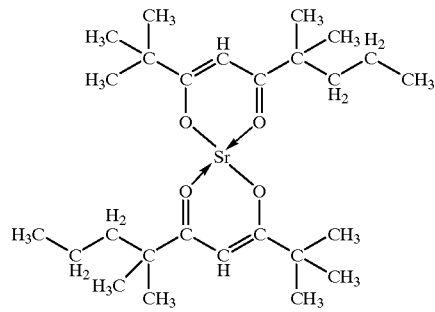

* * * * *